United States Patent [19]

Mueller et al.

[11] Patent Number: 4,792,631
[45] Date of Patent: Dec. 20, 1988

[54] PREPARATION OF DI-TERT.-BUTYLETHYLENEDIAMINE

[75] Inventors: Herbert Mueller, Frankenthal; Walter Mesch, Ludwigshafen, both of Fed. Rep. of Germany

[73] Assignee: BASF Aktiengesellschaft, Ludwigshafen, Fed. Rep. of Germany

[21] Appl. No.: 7,787

[22] Filed: Jan. 28, 1987

[30] Foreign Application Priority Data

Jan. 29, 1986 [DE] Fed. Rep. of Germany ....... 3602527

[51] Int. Cl.$^4$ ...................... C07C 85/08; C07C 85/11
[52] U.S. Cl. .................................... 564/489; 564/473
[58] Field of Search ................................. 564/473, 489

[56] References Cited

U.S. PATENT DOCUMENTS 4,160,785  6/1979  Webb et al. ......................... 564/489

FOREIGN PATENT DOCUMENTS 2048750  4/1972  Fed. Rep. of Germany ...... 564/473

OTHER PUBLICATIONS

Tetrahedron 26, pp. 2555-2560 (1970).

Primary Examiner—Glennon H. Hollrah
Assistant Examiner—John A. Sopp
Attorney, Agent, or Firm—Keil & Weinkauf

[57] ABSTRACT

Di-tert.-butylethylenediamine is prepared by reacting tert.-butylamine with glyoxal to form di-tert.-butylglyoxaldiimine and water and subsequently hydrogenating the diimine by (a) carrying out the reaction of tert.-butylamine with glyoxal in the presence of a hydrocarbon phase,
(b) separating the hydrocarbon with the reaction product from water, and
(c) catalytically hydrogenating the reaction product in the hydrocarbon phase.

14 Claims, No Drawings

PREPARATION OF DI-TERT.-BUTYLETHYLENEDIAMINE

The present invention relates to a process for preparing di-tert.-butylethylenediamine by reacting tert.-butylamine with glyoxal to form di-tert.-butylglyoxaldiimine and water and subsequently hydrogenating the diimine. Di-tert.-butylethylenediamine is a useful intermediate which, for example, can be used as a catalyst in the preparation of polyphenylene oxide resins.

U.S. Pat. No. A-4,160,785 describes a process of the type mentioned at the beginning wherein the reaction is carried out in the presence of methanol. In this form of the process and as also described in Tetrahedron 26 (1970), 2555-60, the diimine is prepared from tert.-butylamine and aqueous glyoxal. Before the hydrogenation the diimine must be isolated from the reaction mixture. The hydrogenation in the process of U.S. Pat. No. A-4,160,785 is carried out in the presence of methanol or ethanol. The crucial feature according to said publication is that a solvent which has a high hydrogen uptake capacity is chosen for the hydrogenation. From the evidence of Table I in Example 3 of said publication, only methanol and ethanol are suitable on that basis. Hydrocarbons such as cyclohexane and benzene are classed as completely unsuitable on the basis of hydrogen uptake capacity. The process of U.S. Pat. No. A-4,160,785 gives yields of the order of 70%. On the evidence of the abovementioned Table I, no hydrogenation yield is obtained on using cyclohexane or benzene.

It is an object of the present invention to provide a process of the type mentioned at the beginning where the stage of reacting tert.-butylamine with glyoxal and the subsequent hydrogenation stage are significantly simplified and improved and higher overall yields are obtainable.

We have found that this object is achieved with a process of the type mentioned at the beginning, which comprises
 (a) carrying out the reaction of tert.-butylamine with glyoxal in the presence of a hydrocarbon phase,
 (b) separating the hydrocarbon with the reaction product from water, and
 (c) catalytically hydrogenating the reaction product in the hydrocarbon phase.

In the preferred embodiment, the tert.-butylamine is dissolved in the hydrocarbon, and the glyoxal is used in aqueous solution.

Suitable hydrocarbons are in particular those which do not undergo hydrogenation under the conditions of hydrogenating the diimine. Preference is given to hydrocarbons which boil within the range from >45° C. to about 160° C., in particular from 60° to 130° C.

Suitable hydrocarbons are large in number. Preference is given to industrially inexpensively available hydrocarbons, for example cyclic hydrocarbons, e.g. cyclohexane, acyclic hydrocarbons, for example gasolines, e.g. higher-boiling gasoline fractions having boiling points of, for example, from 100° to 120° C., and other industrially available hydrocarbon mixtures, for example products such as Skellysolve ®. Particular preference is also given to aromatic hydrocarbons, such as toluene. Xylene is particularly preferred.

According to the invention, it is possible to use not only individual hydrocarbons but also mixtures thereof, as long as the hydrocarbons used are readily separated from di-tert.-butylethylenediamine. This is true in particular when the di-tert.-butylethylenediamine is to be separated off by distillation.

The single-vessel reaction of glyoxal, t-butylamine and hydrocarbon is carried out particularly advantageously by dissolving 2 to 3 mole fractions of amine in from half to twice the amount by weight of hydrocarbon and adding 1 mole fraction of glyoxal in the form of an aqueous, approximately 40–50% strength, solution. The two phases are mixed with a stirrer. At 50° C. the reaction is complete in 2 hours.

The oil phase is then separated from the water. The clear, homogeneous phases separate easily from each other. It can be expedient, for example for the purpose of avoiding a solid hydrate of DTBED, to distil a little, dissolved water out of the oil phase before the hydrogenation. The water is removed together from 5 to 10% of the hydrocarbon used.

The hydrogenation can be carried out continuously or batchwise. If the hydrogenation is carried out batchwise, it is found to be advantageous to work in the presence of a suspension catalyst. If the process is carried out continuously, the use of a supported catalyst is advantageous.

Suitable catalysts are transition metals in general. Particularly suitable catalysts are based on nickel, platinum and palladium. The catalysts may contain customary promoters and other additives.

The first stage of the reaction is expediently carried out at temperatures from room temperature to 150° C. The subsequent hydrogenation is preferably carried out at 50°–150° C., in particular at 60°–80° C.

Expediently pressures of from 10 to 60 bar are employed. In this pressure range the uptake of hydrogen is rapid. It can be necessary to cool the system.

The hydrogenation product is worked up in a conventional manner, in particular by fractional distillation. The workup renders the amine colorless. The product obtained is more than 98% pure. The yield is about 85% of theory.

In the light of U.S. Pat. No. A-4,160,785, it must be regarded as surprising that the process according to the invention and the simple method thereof leads to a pure product in a high yield. The data in U.S. Pat. No. A-4,160,785, in particular Example 3 and Table I, had to prejudice those skilled in the art against the use of hydrocarbons in a process according to the invention. A particularly surprising feature of the process according to the invention is the rapid hydrogen uptake in the hydrogenation stage, which frequently necessitates special cooling. This contrasts particularly sharply with the results in Table I of U.S. Pat. No. A-4,160,785.

In some instances it is possible to increase the yield of di-tert.-butylenediamine to up to 90% of theory by adding a little tert.-butylamine for example about 5% by weight, to the solution of the diimine in the hydrocarbon.

The invention is illustrated in detail by the Examples below.

EXAMPLE 1

To 400 g of gasoline fraction, boiling point 122°–124° C., with n-octane as main constituent are added 483 g of t-butylamine (6.6 g mol). A clear solution forms.

At 45°–50° C., 435 g of 40% strength aqueous glyoxal (3.0 g mol) are added dropwise with stirring. This is followed by one hour of stirring.

The aqueous phase, which has a higher specific density, is then separated in a separating funnel from the oil phase (922 g).

The oil phase is then distilled until all the water has been removed. 18 g of water and 21 g of t-butylamine are obtained in addition to 60 g of gasoline in the form of a two-phase mixture.

The catalyst for the hydrogenation of the oil phase is platinum on carbon (5% strength, 3 g, at 80° C. and 60 bar).

Distillation gives 413 g of di-t-butylenediamine (80% of theory, boiling point 120° C./130 mbar). The product is liquid and, by GC, 98.5% pure.

EXAMPLE 2

To 435 g of o-xylene and 483 g of t-butyleneamine are added at 45°–50° C. 435 g of aqueous 40% strength glyoxal with stirring. After 1 hour the oil phase is separated off, and the aqueous phase is extracted once more with 50 g of xylene.

The combined hydrocarbon phases are then distilled at 130 mbar at a bottom temperature of up to 95° C. to remove 20 g of water.

The hydrogenation is effected with 3 g of platinum on carbon (5% strength) at 70° C. and 60 bar hydrogen pressure. The calculated amount of hydrogen is taken up in two hours.

Distillation gives 450 g of DTBED (87% of theory).

EXAMPLE 3

A solution of t-butylamine in octane is reacted with aqueous glyoxal as described in Example 1. The oil phase is separated off and stripped of water. The hydrogenation catalyst is Raney nickel in octane. It is prepared by sucking water off Raney nickel, washing the residues with methanol and suspending the catalyst in gasoline. The hydrogenation takes place at 60°–80° C. and 60 bar of hydrogen. The yield after purifying distillation is 85% of theory.

We claim:

1. A process for preparing di-tert.-butylethylenediamine by reacting tert.-butylamine with glyoxal to form di-tert.-butylglyoxaldiimine and water and subsequently hydrogenating the diimine, which comprises
    (a) carrying out the reaction of tert.-butylamine with glyoxal in the presence of a hydrocarbon phase,
    (b) separating the hydrocarbon with the reaction product from water, and
    (c) catalytically hydrogenating the reaction product at a temperature of from 50°–150° C. in the hydrocarbon phase.
2. The process of claim 1, wherein the tert.-butylamine is dissolved in hydrocarbon and the glyoxal is used in the form of an aqueous solution.
3. The process of claim 1, wherein the hydrocarbon used is of the type which does not undergo hydrogenation under the conditions of hydrogenating the diimine.
4. The process of claim 1, wherein the hydrocarbon used has a boiling point of from 45° to 160° C.
5. The process as claimed in claim 1, wherein the hydrocarbon used has a boiling point of from 60° to 130° C.
6. The process of claim 1, wherein, if the process is carried out batchwise, the hydrogenation is carried out in the presence of a suspension catalyst.
7. The process of claim 1, wherein, if the process is carried out continuously, a supported catalyst is employed.
8. The process of claim 1, wherein the reaction of the tert.-butylamine with glyoxal is carried out at from room temperature to 150° C.
9. The process of claim 1, wherein the hydrogenation of the diimine is carried out at 60°–80° C.
10. The process of claim 1, wherein a pressure of from 10 to 60 bar is employed.
11. The process of claim 1, wherein the hydrocarbon is one boiling at from 45° C. to about 160° C.
12. The process of claim 1, wherein the hydrocarbon is selected from the group consisting of toluene, xylene, n-octane, cyclohexane, and a gasoline fraction having a boiling point of from 100° to 120° C.
13. The process of claim 1, wherein the hydrocarbon is toluene.
14. The process of claim 1, wherein the hydrocarbon is xylene.

* * * * *